(12) United States Patent
Graf

(10) Patent No.: US 8,620,403 B2
(45) Date of Patent: Dec. 31, 2013

(54) METHOD AND APPARATUS FOR ACQUISITION OF MAGNETIC RESONANCE SLICE IMAGES OF A SUBJECT

(75) Inventor: Gudrun Graf, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1333 days.

(21) Appl. No.: 11/674,235

(22) Filed: Feb. 13, 2007

(65) Prior Publication Data

US 2007/0191703 A1  Aug. 16, 2007

(30) Foreign Application Priority Data

Feb. 15, 2006 (DE) .......................... 10 2006 007 057

(51) Int. Cl.
*A61B 5/055* (2006.01)
*G01V 3/14* (2006.01)
(52) U.S. Cl.
USPC .......................................... 600/410; 324/309
(58) Field of Classification Search
None
See application file for complete search history.

(56) References Cited

U.S. PATENT DOCUMENTS

| | | | | |
|---|---|---|---|---|
| 6,061,420 A * | 5/2000 | Strong et al. | | 378/4 |
| 6,108,573 A * | 8/2000 | Debbins et al. | | 600/410 |
| 6,166,544 A * | 12/2000 | Debbins et al. | | 324/309 |
| 6,195,409 B1 * | 2/2001 | Chang et al. | | 378/20 |
| 6,396,266 B1 * | 5/2002 | Debbins et al. | | 324/307 |
| 6,522,141 B2 | 2/2003 | Debbins et al. | | |
| 6,828,787 B2 | 12/2004 | Oesingmann | | |
| 8,125,222 B2 * | 2/2012 | Sugiura | | 324/307 |
| 8,199,168 B2 * | 6/2012 | Virtue | | 345/642 |
| 2003/0095144 A1 * | 5/2003 | Trevino et al. | | 345/764 |
| 2003/0173965 A1 | 9/2003 | Oesingmann | | |
| 2007/0276221 A1 * | 11/2007 | Warntjes | | 600/410 |
| 2011/0228998 A1 * | 9/2011 | Vaidya et al. | | 382/131 |
| 2012/0010495 A1 * | 1/2012 | de Oliveira et al. | | 600/410 |

FOREIGN PATENT DOCUMENTS

DE  10 2004 026 616 A1  12/2005

OTHER PUBLICATIONS

Shurmann, Martin, MD. "fMRI Guidelines", Brain Research Unit, Helsinki University of TEchnology, May 15, 2004.*

* cited by examiner

*Primary Examiner* — Long V. Le
*Assistant Examiner* — Angela M Hoffa
(74) *Attorney, Agent, or Firm* — Schiff Hardin LLP

(57) ABSTRACT

In a method for acquisition of magnetic resonance slice images of an examination subject of a patient by using a magnetic resonance apparatus having a control device controlling the image acquisition operation, wherein the slice images are acquired as slice image stacks situated in different planes in a field of view within a homogeneous magnetic field, wherein the control device determines the volume of the examination subject using an overview image exposure and, dependent on the determination result, at least one or more of the image acquisition parameters of slice thickness, slice interval, slice count and/or size of the field of view is adapted.

4 Claims, 1 Drawing Sheet

| | Adaptation | from - to |
|---|---|---|
| Slice thickness | ✓ | 9-11 |
| Slice interval | ✓ | 0,6-1,2 |
| Slice count | ☐ | |
| Field of View | ✓ | |

Control Device

METHOD AND APPARATUS FOR ACQUISITION OF MAGNETIC RESONANCE SLICE IMAGES OF A SUBJECT

BACKGROUND OF THE INVENTION

1. Field of the Invention

The present invention concerns a method for acquisition of magnetic resonance slice images of an examination subject of a patient by means of a magnetic resonance apparatus having a control device controlling the image acquisition operation, whereby the slice images being acquired as slice image stacks situated in different planes in a field of view within a homogeneous magnetic field.

2. Description of the Prior Art

Slice images of an examination subject of a patient can be acquired in high-resolution form by a magnetic resonance apparatus. The patient is exposed to a homogeneous magnetic field. Further radio-frequency magnetic field, namely gradient fields that serve for spatial resolution, and a radio-frequency field, causing magnetic resonance signals to be generated in the examination subject that are detected and used for image generation. The basic manner of operation of such a magnetic resonance apparatus is well known and need not be described in more detail herein.

Magnetic resonance data from an examination subject are typically acquired in the form of a number of individual slice images. These slice images lie atop one another in different levels, frequently separated by a very narrow gap; thus consequently with a defined separation. The slice images themselves, which are aligned with regard to a specific anatomical structure, typically lie parallel to one another. Such a slice image stack thus provides image information from various levels of the examination subject. A total image of an examination subject is typically acquired with a previously-defined number of individual slice images, the slice thickness and the possibly-defined gap being also set in advance. In brain acquisitions, 19 individual slice images are acquired; the slice thickness is, for example, 10 mm with a gap of 1 mm. Such acquisition parameters are frequently set in advance for a brain acquisition. Corresponding parameter sets also exist for acquisition of other examination regions, such as organs or bones or the like.

The size of the examination subject frequently varies considerably dependent on the patient size. The brain of a small child is distinctly smaller than that of an adult; bone structures (for example joint or innominate bones) vary significantly in their size from child to adult. If (with regard to the example of a brain acquisition) the brain of an small child is examined with the same slice count, the same slice thickness and the same gap as the parameters are defined for the brain acquisition of an adult, some slices will inevitably no longer measure in the brain but rather outside of the brain. This image information consequently does not contribute to the imaging of the actual examination subject. In reverse, if the brain of an adult is acquired starting from the parameters relating to the size of the child's brain, the entire brain inevitably will not be imaged since this is distinctly larger than the child's brain, for which optimal coverage requires the acquisition parameters to be defined. The acquisition of a brain is only an example. These problems result in equal measure given the acquisition of other examination subjects where considerable size differences are present, in particular, for example, in the acquisition of structures (such as the bones) varying significantly as a result of growth.

In order to address this problem, the operator of a magnetic resonance data acquisition apparatus has previously been required to manually set the slice thickness and/or the slice interval (gap) (typically starting from an unchanged slice count) in order to define an optimal slice coverage with regard to the real size of the examination subject. The slice count is typically retained since as few parameters as possible are changed by the operator for adaptation to the examination subject and a high image count is desired. This manual adaptation is not only laborious and time-consuming but also possibly incorrect (such as in the case of a wrong parameter setting), such that the subsequent image acquisition is not usable or not completely usable.

SUMMARY OF THE INVENTION

An object of the present invention is to provide a method that is improved and unburdens the operator.

This object is achieved in accordance with the invention by a method of the aforementioned type wherein the control device determines the volume of an examination subject using an overview image exposure of the examination subject and, dependent on the determination result, adapts one or more of the image acquisition parameters slice thickness, slice interval, slice count and/or size of the field of view.

In the inventive method, an automatically implemented determination of the three-dimensional volume of the examination subject ensues using an overview image of the examination subject typically acquired anyway before the actual measurement. In the example of a brain acquisition, the brain volume (consequently thus also the spatial extent thereof) is thus determined using the overview image. Dependent on the knowledge of the size and position of the examination subject resulting from this determination relative to the coordinate system of the magnetic resonance apparatus, one or more of the central image acquisition parameters is now automatically adapted dependent on the determined volume. The control device thus automatically varies the slice thickness, the slice interval, the slice count and/or the size of the field of view (thus the length x of the respectively acquired slice image) in order to determine (using this parameter setting) the optimal coverage with regard to the determined real volume or the determined real size in connection with the real position of the subject.

The operator thus is no longer required to be active; but instead the parameter setting ensues automatically by determination of the optimized image acquisition parameters by the control device, dependent on the subject information acquired from the overview image. An optimal subject coverage is thereby ensured and incorrect settings are advantageously avoided.

The adaptable image acquisition parameter or parameters can be determined by the operator via an input unit. In this embodiment of the invention, the operator is given the possibility to define which of the aforementioned central image acquisition parameter or parameters can be altered or set at all in the framework of the inventive parameter adaptation. For example, if the operator would like to leave the slice count unchanged at, for example 19 (with regard to the example of the brain acquisition) and if, for example, the field of view should also not be altered, the operator can thus select and define this on a monitor via a suitable input unit such as a keyboard or the like. The control device then is permissible to still vary the parameters slice thickness and slice interval in order to determine, with regard to the real volume or the real size of the examination subject) the optical parameter settings relative to these operator specifications. The operator can thereby define an arbitrary parameter combination as adaptable, or can exclude an arbitrary parameter combination from the adaptation.

Furthermore, it is possible that an upper limit and/or a lower limit can be determined on the part of the operator with regard to one or more adaptable image acquisition parameters. This also occurs through a suitable input unit in connection with an input mask on a monitor. For example, when the operator allows an adaptability of the slice count, the operator can specify that the maximum and minimum slice count can vary only between an upper limit and a lower limit. Starting from the example of the image acquisition with a typical slice count of 19, the operator can now specify that a maximum of twenty and a minimum of eighteen slices may be acquired. The operator can similarly specify upper and lower limits for slice thickness, for example (in the case of a typical 10 mm-thick slice) a lower limit of 8 mm and an upper limit of 12 mm. The control device varies or seeks the parameter combination that, under consideration of these upper and/or lower limits, offers the optimal coverage in connection with the other given specifications of the operator with regard to the fundamental adaptability of one or more image acquisition parameters.

The inventive method thus allows a largely automatic operation for adaptation of the optimal image acquisition parameters without manual adaptation activity on the part of the operator. If this inventive method or this functionality is integrated, for example, into an auto-align mode of a magnetic resonance apparatus (which mode is an operating mode for automatic adaptation of the measurement for a specific anatomical question), this auto-align functionality can be further expanded. This auto-align functionality already allows a largely automated operation of the magnetic resonance apparatus without more complex operator activity. The operator must merely (if necessary) define the type of the desired image acquisition or, respectively, measurement sequence and (if necessary) the examination subject; otherwise the operation of the magnetic resonance apparatus in auto-align mode is essentially automatically controlled by the control device. The inventive method can provide a further advantageous functionality within this auto-align mode.

In addition to the inventive method, the invention also concerns a magnetic resonance apparatus having a control device controlling the image acquisition operation, whereby the slice images being acquired as slice image stacks situated in different levels in a field of view within a homogeneous magnetic field, the control device being fashioned for implementation of the method as described above.

DESCRIPTION OF THE PREFERRED EMBODIMENTS

Figure 1:
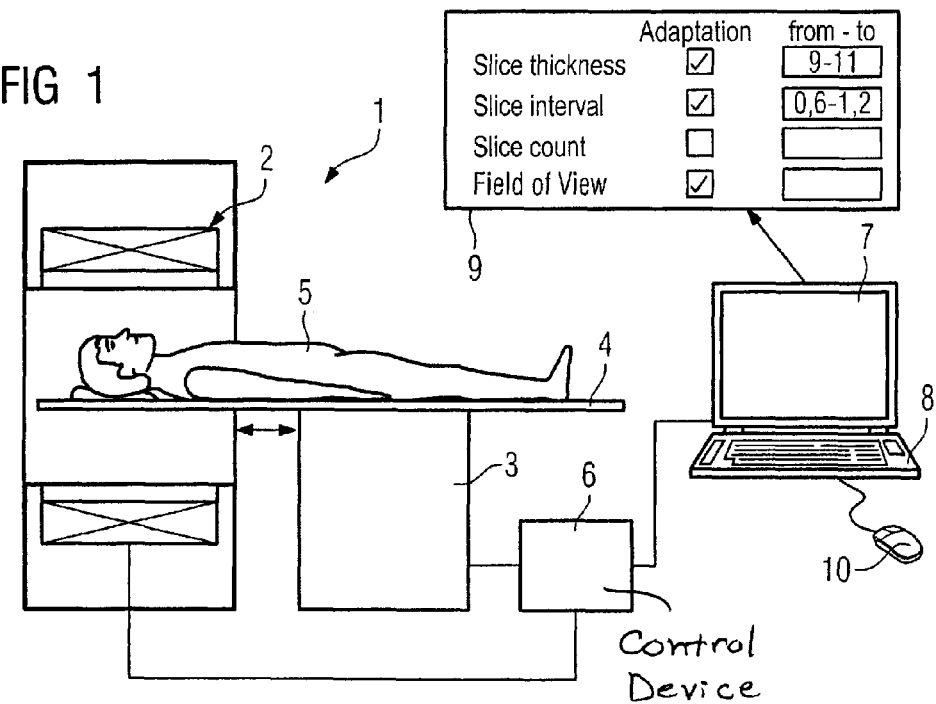
FIG. 1 is a basic block diagram of an inventive magnetic resonance apparatus for implementation of the inventive method.

FIG. 1 shows an inventive magnetic resonance apparatus 1 having a magnetic field generation device 2 that serves for the generation of a homogeneous magnetic field as well as the generation of the gradient and magnetic fields. Different magnets or coil components are typically used for these purposes; but for simplicity, only a central magnetic field generation device.

The magnetic resonance apparatus 1 also has a patient table 3 with a tabletop 4 on which a patient 5 lies in the shown example. Also provided is a control device 6 that controls the operation of the magnetic resonance apparatus 1 and thus the magnetic field generation device 2 and the patient table 3, which is variable in terms of height, and the tabletop can be displaced (shown by the double arrow). A monitor 7 as well as an input unit 8 (here a keyboard) are associated with the control device 6. Suitable commands (also falling in this category are image acquisition parameters) can be input and defined on the monitor 7 via the input unit 8 as the slice images acquired in the framework of the image acquisition are output on the monitor 7 (the slice images being acquired in the form of the received magnetic resonance signals that are processed, and the images are generated by the control device 6 which for this possesses an image processing device).

For acquisition of data from the examination subject, the operator can automatically define variable (with regard to the real subject size) image acquisition parameters via the monitor 7. Shown enlarged is an input mask 9 as it is displayed on the monitor 7. Here the slice thickness, the slice interval, the slice count as well as the size of the field of view are specified as central image acquisition parameters that can be varied in principle. In a first input row "Adaptation" the operator can select via the input unit 8 (for example, using its associated mouse 10 in connection with a screen cursor) in respective boxes whether this parameter may be adapted (consequently thus may be altered) or not. In the shown example, the operator has defined that the slice thickness, the slice interval as well as the size of the field of view may be varied but not the slice count. The variation possibility refers to an image acquisition parameter set defined in advance. With regard to the example of a selected brain acquisition, this can, for example, define 10 mm as the slice thickness, 1 mm as the slice interval, 19 as the slice count and 40 cm as the size of the field of view given a present length or, respectively, a present diameter of the (typically spherical) homogeneous magnetic field of likewise 40 cm.

In a second row "from-to", the operator can now define upper and/or lower limits with regard to the image acquisition parameters respectively selected by the operator as adaptable in principle. The operator has effected this with regard to the acquisition parameters slice thickness and slice interval. Assuming, for example, a basic parameter of 10 mm, the slice thickness should be able to be varied at a maximum between 9 mm as a lower limit and 11 mm as an upper limit. Assuming 1 mm as a basic parameter, the slice interval should correspondingly be capable of being varied between 0.6 mm and 1.2 mm. The field of view is in fact adaptable in principle, but without upper and lower limits. The operator wants to retain the slice count; the operator has defined it as not variable so it should be unchanged at, for example, 19.

After an overview image of the examination subject (in the described example the brain) was acquired in advance, the control device 6 now determines the real size or the real volume of the brain. The control device 6 thus determines which volume or which anatomical shape is in principle to be covered with the individual slice images and how this volume is situated in the coordinate system of the magnetic resonance apparatus 1. If this is known, in the next step the position of the individual slice planes is automatically defined by the control device relative to the examination subject (here the brain). The plane position conforms to specific anatomical structures in the brain that the control device 6 finds automatically and defines the plane along or relative to these anatomical structures. If the plane position is also defined, the adaptation of the adaptable parameters ensues in order to ensure an optimal subject coverage. If it is a small brain, the control device will reduce the variable parameters because the slice count may not be varied. This means that the slice thickness is reduced, for example, to 9 mm, the slice interval is reduced, for example, to 0.7 mm, the field of view is reduced, for example, from 40 cm to 35 cm. If the examination subject is a large examination subject, the parameters are correspondingly selected differently.

As soon as the image acquisition parameter set is now defined, the measurement can ensue on the basis of these image acquisition parameters. The control device now controls the operation of the magnetic field generation device, acquires the corresponding magnetic resonance signals and processes these to form the slice images to be output, which slice images are then shown on the monitor 7.

Figure 2:
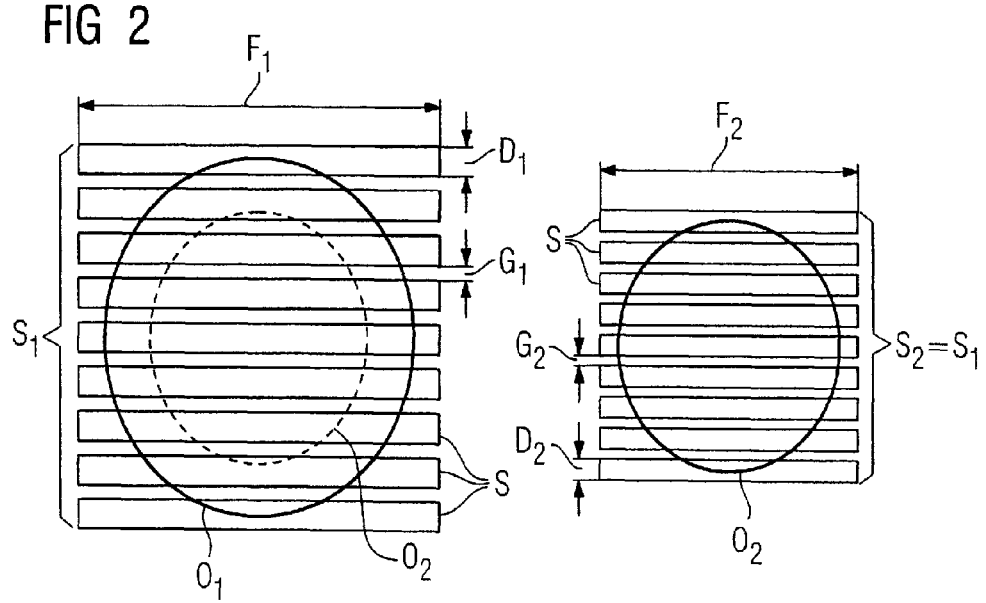
FIG. 2 shows two differently-sized examination subjects and the image acquisition parameters correspondingly adapted dependent on the subject sizes in accordance with the present invention.

FIG. 2 shows an example of an inventively varying subject coverage. A large subject $O_1$ (exemplarily an oval) is shown to the left in FIG. 2. It is assumed that this is hereby a brain. Here nine slices S in total in which corresponding slice images are acquired are exemplarily drawn. In total here a slice count $S_1=9$ thus results here. The slice thickness is $D_1$, the slice interval (gap) is $G_1$. The size of the field of view is $F_1$. An optimal subject coverage can apparently be ensured via the nine slices given a present slice thickness $D_1$, present slice interval $G_1$ and present field of view $F_1$. Essentially only image information of the subject and only barely image information from surrounding regions are acquired.

In comparison to this, to the right FIG. 2 shows a smaller subject $O_2$, assumedly a distinctly smaller brain in the described exemplary embodiment. Here as well as a plurality of slices S are defined again. The slice count $S_2$ is likewise nine, thus equal to the slice count $S_1$, in order to conform to the example according to FIG. 1 where the slice count was defined as invariable. The slice interval $D_2$ clearly decreases, meaning that $D_2<D_1$. The same correspondingly applies for the slice interval $G_2$ which is likewise smaller than the slice interval $G_1$, meaning that $G_2<G_1$. Finally, the field of view $F_2$ was also reduced, meaning that $F_2<F_1$.

Given a constant slice count an optimal subject coverage also clearly results here. Here it is also ensured that only an insignificant portion of the image signals from the regions outside of the subject $O_2$ are acquired. This means that the percentile subject coverage is also optimally selected here. For comparison purposes, the subject $O_2$ in the left representation is drawn relative to the subject $O_1$. If one were to measure the subject $O_2$ with the image acquisition parameters that form the basis of the measurement of the subject $O_1$, it would result that a large proportion of the acquired image signals would be acquired outside of the subject $O_2$. As is generally known, these image signals do not contribute to the image representation of the subject, thus are irrelevant with regard to the image acquisition and diagnostics.

It should be noted in conclusion that the acquisition of a brain described in the described embodiment is only an example. The subjects $O_1$ and $O_2$ can be any anatomical subjects or structures of the human body. The inventive method is especially applied to such anatomical structures or subjects that can distinctly vary from patient to patient dependent on the patient size. Bone or skeletal structures, are examples. A prominent example is the region of the innominate bones or, respectively, hip joint bones that vary very significantly in terms of their size between a small child and an adult. For example, the same similarly applies for the upper and lower femur or the spinal column etc.

Although modifications and changes may be suggested by those skilled in the art, it is the intention of the inventor to embody within the patent warranted hereon all changes and modifications as reasonably and properly come within the scope of her contribution to the art.

I claim as my invention:

1. A method for acquiring magnetic resonance (MR) slice images of an examination subject, comprising the steps of:
   providing a computerized processor with an overview MR image exposure of an examination subject in a coordinate system of an MR data acquisition unit with which the overview MR image exposure was acquired, said MR data acquisition unit generating a magnetic field that is sufficiently homogenous to acquire diagnostic MR data only within a known homogeneity volume of the MR data acquisition unit;
   in said processor, from said overview MR image exposure, automatically determining a volume in said coordinate system of the subject and, dependent on said volume, automatically determining at least one stack-defining image acquisition parameter that defines a slice image stack, consisting of multiple individual slice images, respectively representing multiple slices of the examination subject, that causes all of the slices respectively represented by said slice images in said slice image stack to be situated in respectively different planes that are within said homogeneity volume of said MR data acquisition unit, said stack-defining parameter being selected from the group consisting of, for said individual multiple slices, a slice thickness, a slice interval, and a slice count; and
   from said processor, controlling operation of said MR data acquisition unit according to said stack-defining parameter to acquire MR data in said coordinate system for said slice images in said slice image stack according to an MR data acquisition parameter set that includes said stack-defining parameter, with all of said slices being situated in said respectively different planes in said homogeneity volume of said MR data acquisition unit.

2. A method as claimed in claim 1 comprising allowing manual selection, via said computerized processor of at least one adaptable image acquisition parameter in said MR data acquisition parameter set, in addition to said slice-defining parameter.

3. A method as claimed in claim 2 comprising, for each adaptable image acquisition parameter, allowing manual selection of at least one of an upper limit and a lower limit therefor.

4. A magnetic resonance apparatus comprising:
   a magnetic resonance data acquisition unit adapted to interact with a subject to acquire magnetic resonance data therefrom in a coordinate system of the MR data acquisition unit with which an overview MR image exposure was acquired, said MR data acquisition unit generating a magnetic field that is sufficiently homogenous to acquire diagnostic MR data only within a known homogeneity volume of the MR data acquisition unit;
   a control unit configured to operate said MR data acquisition unit to acquire the overview MR image exposure of the subject in said coordinate system, said control unit being configured to automatically determine a volume in said coordinate system of the subject using the overview MR image exposure and, dependent on said volume, to automatically determine at least one stack-defining image acquisition parameter that defines a slice image stack, consisting of multiple individual slice images, respectively representing multiple slices of the examination subject, that causes all of the slices respectively represented by said slice images in slice image stack to be situated in different planes that are within said homogeneity volume of said MR data acquisition unit, said stack-defining parameter being selected from the group consisting of, for said individual multiple slices, a slice thickness, a slice interval, and a slice count; and said control unit being configured to operate said MR data acquisition unit to acquire MR data in said coordinate system for the multiple individual images in said slice image stack according to an MR data acquisition parameter set that includes said stack-defining parameter, with all of said slices being situated in said respectively different planes within said homogeneity volume of said MR data acquisition unit.

\* \* \* \* \*